(12) United States Patent
Prakash et al.

(10) Patent No.: US 6,506,905 B1
(45) Date of Patent: *Jan. 14, 2003

(54) METHOD OF PREPARATION OF PACLITAXEL (TAXOL) USING 3-(ALK-2-YNYLOXY) CARBONYL-5-OXAZOLIDINE CARBOXYLIC ACID

(75) Inventors: Sharma Arun Prakash, Kalyani (IN); Sarkar Subrata, Kalyani (IN)

(73) Assignee: Dabur India Limited, Nadia (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/870,942

(22) Filed: Jun. 1, 2001

(51) Int. Cl.⁷ ............................................. C07D 263/06
(52) U.S. Cl. ........................ 548/215; 548/225; 548/226; 548/229; 549/510
(58) Field of Search ................................ 548/215, 225, 548/226, 229; 549/510

(56) References Cited

U.S. PATENT DOCUMENTS 5,906,990 A * 5/1999 Bouchard et al. ............ 514/449
6,150,537 A * 11/2000 Liotta et al. ................. 549/214
6,265,587 B1 * 7/2001 Chanteloup et al. ........ 548/237

* cited by examiner

Primary Examiner—Joseph K. McKane
Assistant Examiner—Kamal Saeed
(74) Attorney, Agent, or Firm—Venable; George H. Spencer; Ashley J. Wells

(57) ABSTRACT

3-(alk-2-ynyloxy)carbonyl-5-oxazolidine carboxylic acid and its analogs having a formula

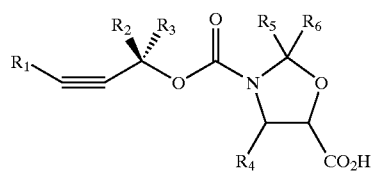

and wherein $R_1$ is hydrogen, aryl, heteroaryl, alkyl, alkenyl, alkynyl, $R_2$ and $R_3$ are independently selected from hydrogen, alkyl, alkenyl, alkynyl, aryl, heteroaryl, $R_4$ is hydrogen, alkyl, alkenyl, alkynyl, aryl, substituted aryl, heteroaryl, $R_5$ and $R_6$ independently selected from hydrogen, alkyl, alkenyl,alkynyl, arly, heteroaryl, alkoxy, alkeyloxy, alkynyloxy, aryloxy, heteroaryloxy.

25 Claims, No Drawings

METHOD OF PREPARATION OF PACLITAXEL (TAXOL) USING 3-(ALK-2-YNYLOXY) CARBONYL-5-OXAZOLIDINE CARBOXYLIC ACID

FIELD OF THE INVENTION

The present invention relates to a novel oxazolidine carboxylic acid and a process for its preparation. The invention further relates to a process for the preparaton of paclitaxel (taxol) using such oxazolidine carboxylic acid. Paclitaxel (Taxol) (1) is a terpene of taxane family and has the formula shown below and has an application for treatment of various types of cancer. Non-natural analog of paclitaxel (taxol), docetaxel (taxotere) (2) is also an approved anticancer drug. Thus, there is great interest in molecules having similar structures for development of new anticancer drugs and SAR studies.

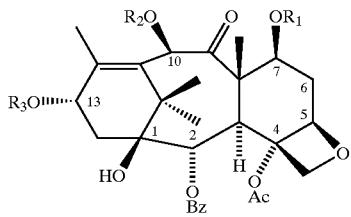

1. Taxol $R_1$=H, $R_2$=Ac, $R_3$=

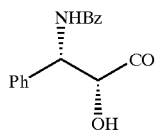

2. Taxotere $R_1$=$R_2$=H, $R_3$=

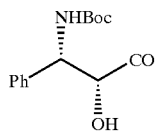

3. Baccatin $R_1$=$R_3$=H, $R_2$=Ac
4. 10-Deacetylbacctin (DAB) $R_1$=$R_2$=$R_3$H

BACKGROUND OF THE INVENTION

The structure of paclitaxel (taxol) has two distinct units. One is baccatin (3) and other is N-benzoylphenylisoserine, the side chain, connected to baccatin at C-13 through ester linkage. It has been shown that the -amido-hydroxy ester side chain at C-13 is very essential for anticancer activity of taxol and any other taxol analogs. The supply of taxol from natural sources is very limited and so there is great interest in its synthesis. 10-deacetyl baccatin (4) is more readily available than taxol from the leaves of yew tree and comprises a starting material for semisynthesis of taxol and taxol analogs. It is known in the literature, that it is very difficult to esterify 13 hydroxy of bacctin with -amido-hydroxy carboxylic acid. The difficulty has been ascribed to spatial disposition of 13 hydroxy in the baccatin nucleus. Therefore, considerable efforts have been made to find precursors of -amido-hydroxy carboxylic acid which can be coupled with bacctin in high yield and the resultant couple product can be processed to afford 13-O-(-amido-hydroxycarbonyl) baccatin in high yield and purity.

The following types of cyclic derivative of phenylisoserine are known to couple with 13-hydroxy of baccatin.

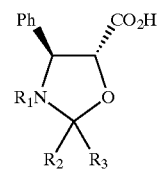

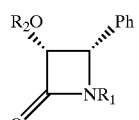

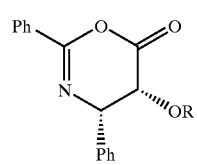

R, $R_1$, $R_2$ and $R_3$=Protecting groups

In the literature, various protecting groups, $R_1$, are described in oxazolidinecarboxylic acid (5). However, alk-2-ynyloxycarbonyl group have not been described so far; The utility of this group over other commonly used protecting groups lies in the fact that this group can be cleaved under neutral condition. All other known protecting groups ($R_1$) are cleaved under either acidic conditions or by hydrogenolysis. The subsequent cleavage of protecting groups $R_2$ and $R_3$ are normally very fast, once $R_1$ is cleaved. Since the baccatin part of taxol is very prone to degradation even under mild acidic or basic conditions, removal of alk-2-ynyloxycarbonyl group under neutral condition facilitates the conversion of taxol intermediate such as 10 to taxol in high yield and high purity.

OBJECTS OF THE INVENTION

An object of this invention is to propose a novel oxazolidine carboxylic acid and a process for the preparation thereof.

Another object of this invention is to propose oxazolidine carboxylic acid which can advantageously be used in the preparation of anticancer drugs.

Still another object of this invention is to propose a process for the preparation of taxol and its synthetic analogs using the proposed oxazolidine carboxylic acid.

DESCRIPTION OF THE INVENTION

The present invention is directed to 3-(alk-2-ynyloxy) carbonyl-5-oxazolidine carboxylic acid and its analogs having a formula

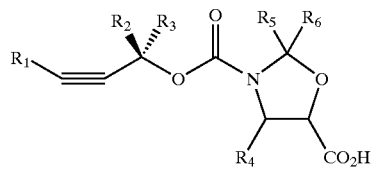

and wherein $R_1$ is hydrogen, aryl, heteroaryl, alkyl alkenyl, alkynyl, $R_2$ and $R_3$ are independently selected from hydrogen, alkyl, alkenyl, alkynyl, aryl, heteroaryl; $R_4$ is hydrogen, alkyl, alkenyl, alkynyl, aryl, substituted aryl, heteroaryl. $R_5$ and $R_6$ independently selected from hydrogen, alkyl, alkenyl, alkynyl, arly, heteroaryl, alkoxy, alkeyloxy, alkynyloxy, aryloxy, heteroaryloxy.

The oxazoldine alkyl groups either alone or with the variable substituents defined above are preferably lower alkyl containing from one to six carbon atoms in the principal chain and up to 10 carbon atoms. They may be straight or branched chain and include methyl, ethyl, propyl, isopropyl, butyl, isobutyl, tert-butyl, pentyl, hexyl and the like. The alkyl part of alkoxy groups defined above are same as a alkyl groups.

The oxazoldine alkenyl groups either alone or with the various substituents defined above are preferably lower alkenyl containing from two to six carbon atoms in the principal chain and up to 10 carbon atoms. They may be straight chain and include ethenyl, propenyl, isopropenyl butenyl, isobutenyl, pentenyl, hexenyl, and the like. The alkenyl part of alkenyloxy groups defined above are same as a alkenyl groups.

The oxazoldine alknyl groups, either along or with the various substituents defined above are preferably lower alkynyl containing from two to six carbon atoms in the principal chain and up to 10 carbon atoms. They may be straight chain and include ethynyl, propynyl, butynyl, isobutynyl, pentynyl, hexynyl and the like. The alkynyl part of alkynyloxy groups defined above are same alkynyl groups.

The oxazoldine aryl moieties eiher alone or with various substituents contain from 6 to 10 carbon atoms and include pheny, -naphthyl etc. substituents include alkanoxy, hydroxy, halogen, alkyl, aryl, alkenyl, acyl, acyloxy, nitro, amino; amido etc.

As defined herein, the term aryloxy includes aromatic heterocyclic moieties the term aryl includes any compound having an aromatic ring of which no hetero atom is a member, and the term heteroaryl includes any compound having an aromatic ring which comprises a hetero atom.

Most preferably, the oxazolidine carboxylic acid has a formula wherein $R_1$, $R_2$ and $R_3$ are hydrogen, $R_4$ is phenyl and $R_5$ and $R_6$ are methyl.

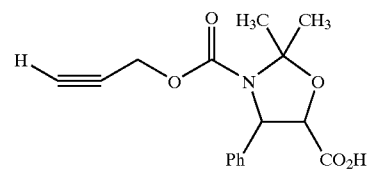

The present invention also describes process of preparation of 3-(alk-2-ynyloxy)carbonyl-5-oxazolidine carboxylic acid and its analogs.

The present invention also describes the preparation of taxol intermediates of following structural formula:

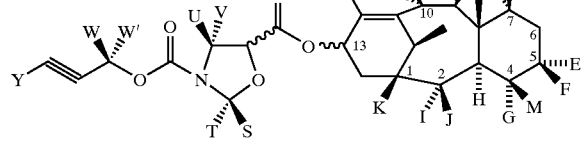

wherein

A and B are independently hydrogen or lower alkanoyloxy, alkenoyloxy, alkynoyloxy aryloyloxy or; A and B together form an oxo;

L and D are independently hydrogen on hydroxy or lower alkanoyloxy, alkenoyloxy, alkynoyloxy, aryloyloxy alkoxycarbonyloxy, aryloxycarbonyloxy or alkylsilyloxy;

E and F are independently hydrogen or lower alkanoyloxy, alkenoyloxy, alkynoyloxy aryloyloxy; or E and F together form an oxo;

G is hydrogen or hydroxy or lower alkanoyloxy, alkenoyloxy, alkynoyloxy, or aryloyloxy or;

G and M together form an oxo or methylene or oxirane ring or

M and F together form an oxetane ring;

J is hydrogen or hydroxy or lower alkanoyloxy, alkenoyloxy, alkynoyloxy, or aryloyloxy or I is hydrogen or hydroxy or lower alkanoyloxy, alkenoyloxy, alkynoyloxy, or aryloyloxy; or I and J together form an oxo; and K is hydrogen or hydroxy, lower alkoxy, alkenoyloxy, alkenoyloxy, alkynoyloxy, or aryloyloxy P and Q are independently hydrogen or hydroxy, or lower alkanoyloxy, alkenoyloxy, alkynoyloxy, aryloyloxy, alkoxycarbonyloxy, aryloxycarbonyloxy or alkylsilyloxy or P and Q together form an oxo; and S and T are independently hydrogen, lower alkyl, alkoxy, alkenyl, alkynyl, aryl, aryloxy, substituted aryl or substituted aryloxy; and U and V are independently hydrogen or lower alkyl, alkenyl, alkynyl, aryl or substituted aryl or heteroaryl and W and W' are independently hydrogen or lower alkyl, aryl or substituted aryl; and Y is hydrogen or lower alkyl, aryl or substituted aryl.

The present invention also describes the preparation of taxol intermediates, natural taxol and non-natural occurring taxols of following structural formula:

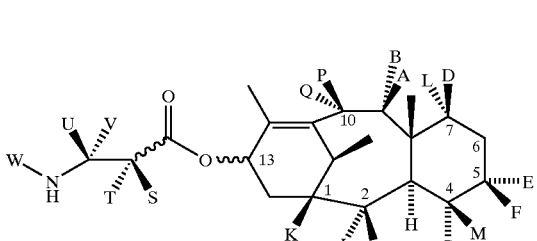

wherein
- A and B are independently hydrogen or lower alkanoyloxy, alkenoyloxy, alkynoyloxy, aryloyloxy, or;
- A and B together form an oxo;
- L and D are independently hydrogen or hydroxy or lower alkanoyloxy, alkenoyloxy, alkynoyloxy, aryloyloxy, alkoxycarbonyloxy, aryloxycarbonyloxy or alkylsilyloxy;
- E and F are independently hydrogen or lower alkanoyloxy, alkenoyloxy, alkynoyloxy, aryloyloxy; or
- E and F together form an oxo;
- G is hydrogen or hydroxy or lower alkanoyloxy, alkenoyloxy, alkynoyloxy, or aryloyloxy or;
- G and M together form; an oxo or methylene or oxirane ring or M and F together form an oxetane ring;
- J is hydrogen or hydroxy or lower alkanoyloxy, alkenoyloxy, alkynoyloxy, or aryloyloxy or
- I is hydrogen or hydroxy or lower alkanoyloxy, alkenoyloxy, alkynoyloxy, or aryloyloxy; or
- I and J together form an oxo; and
- K is hydrogen or hydroxy, lower alkoxy, alkanoyloxy, alkenoyloxy, alkynoyloxy, or aryloyloxy
- P and Q are independently hydrogen or hydroxy or lower alkanoyloxy, alkenoyloxy, alkynoyloxy, aryloyloxy or alkoxycarbonyloxy, aryloxycarbonyloxy or alkylsilyloxy
- P and Q together form an oxo; and
- S and T are independently hydroxy, alkoxy, aryloxy, or lower alkanoyloxy, alkenoyloxy, alkynoyloxy, or aryloyloxy; and
- U and V are independently hydrogen or lower alkyl, alkenyl, alkynyl, aryl or substituted aryl or heteroaryl and
- W is hydrogen, alkanoyl, alkenoyl, alkynoyl, aryloyl, heteroaryloyl, alkoxycarbonyl, aryloxycarbonyl, heteroaryloxycarbonyl.

The taxol alkyl groups either alone or with the variable substituents defined above are preferably lower alkyl containing from one to six carbon atoms in the principal chain and up to 10 carbon atoms. They may be straight or branched chain such as methyl, ethyl, propyl, isopropyl, butyl, isobutyl, tert-butyl, pentyl, hexyl and the like. The taxol alkenyl groups either alone or with the various substituents defined above are preferably lower alkenyl containing from two to six carbon atoms in the principal chain and up to 10 carbon atoms. They may be straight or, branched chain and include ethenyl, propenyl, isopropenyl, butenyl, isobutenyl, pentenyl hexenyl, and the like.

The taxol alkynyl groups, either along or with the various substituents defined above are preferably lower alkynyl containing from two to six carbon atoms in the principal chain and up to 10 carbon atoms. They may be straight chain and include ethynyl, propynyl, butynyl, isobutynyl, pentynyl hexynyl and the like.

Exemplary alkanoyloxy include acetate, propionate, butyrate, valarate, isobutyrate and the like, the more preferred alkanoyloxy is acetate.

The taxol aryl moieties either alone or with various substituents contain from 6 to 10 carbon atoms and include phenyl, -naphthyl etc. Substituents include alkanoxy, hydroxy, halogen, alkyl, aryl, alkenyl, acyl, acyloxy, nitro, amino; amido etc. phenyl is the more preferred aryl.

As defined herein, the term aryloyloxy includes aromatic heterocyclic moieties, the term aryl includes any compound having an aromatic ring of which no hetero atom is a member, and the term heteroaryl includes any compound having an aromatic ring which comprises a hetero atom.

Preferred values of the substituents A, B, D, L, E, F, G, M, I, J, K, P, Q, S, T, U, V, W, X and Y are enumerated below in Table-1

| | | | | | |
|---|---|---|---|---|---|
| A and B together Form an oxo | A = H B = OAc | A = OAc B = H | A = B = H | | |
| D = OH L = H | D = H L = OH | D = OCOOC H$_2$CCl$_3$ L = H | D = H L = OCOOCH$_2$ CCl$_3$ | D = OCOR L = H | D = L = H |
| E = H F = OAc | E = OAc F = O H | E and F together form an oxo | E = H F = O (oxetane) | | |
| G AND M = CH$_2$ | G = CH$_2$ M = O (Epoxide) | G = O M = CH$_2$ (Epoxide) | G and M together form an oxo | G = OAc M = CH$_2$O (Oxetane) | G = H M = CH$_2$O (Oxetane) |
| I = J = O | I = J = H | I = OCOPh J = H | I = OCOR J = H | | |
| K = H P = OH Q = H | K = OH P = H Q = OH | K = OCOR P = OCOCH$_2$ CCl$_3$ Q = H | K = OCOR P = H Q = OCOCH$_2$ CCl$_3$ | P = OCOR Q = H | P = Q = H |
| S = T = CH$_3$ U = Ar V = H | S = H T = Ar U = H V = Ar | S = H T = OR | S = OR T = H | S = OH T = H | S = H T = OH |
| Structure-10 | W = H W' = H | W = CH$_3$ W' = CH$_3$ | W = H W' = CH$_3$ | W = CH$_3$ W' = H | W = Ar W' = H | W = H W' = Ar |
| Structure-11 | W = H | W = CH$_3$ | W = COAr | W = COOt Bu | | |
| Structure-10 | Y = H | Y = CH$_3$ | Y-Ar | | | |

According to this invention, there is provided a process for the preparation of 3(alk-2-ynyloxy)carbonyl-5-oxazolidine carboxylic acid. The process is illustrated in reaction 1:

SCHEME 1

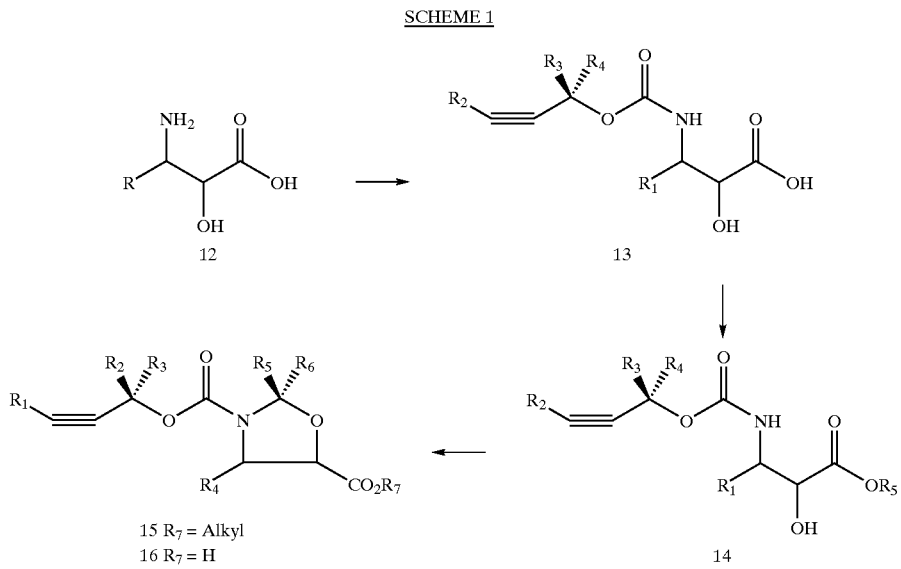

In this process, isoserine 12 is the starting material. In the preferred starting material, R is aryl and the most preferred R is phenyl. The arylisoserine has two asymmetric carbons, all optically active forms such as enantiomers, diastereomers, racemic mixtures and other mixtures are contemplated here. The preferred optically active form of pheneylisoserine is 2R, 3S. This phenylisoserine is commercially available.

Thus, phenylisoserine is condensed with alk-2-ynyl haloformate in presence of some base such as alkali hydroxide or carbonate or bicarbonate or any other acid neutralising chemical. Herein, alk-2-ynyl groups, either alone or with the various substitutents defined above are preferably lower alk-2-ynyl containing from three to six carbon atoms in the principal chain and up to 10 carbon atoms and include but-2-ynyl, pent-2-ynyl, prop-2-ynyl, hex-2-ynyl and the like.

The most preferred haloformate is prop-2-ynyl chloroformate which is available commercially. This can be prepared from diphosgene/triphosgene and propargyl alcohol following the procedure given in Helv.Chim.Acta. Vol 77, 561, 1994.

The most preferred base here is sodium bicarbonate. The condensation is carried out by addition of chloroformate into a solution of isoserine in aqueous bicarbonate over a period of 5–30 min, most preferably over 10–15 min. The acidification of the reaction mixture affords the N-(alk-2-ynyloxy) carbonylisoserine 13. The most preferred one is where $R_1$ is phenyl, $R_2$, $R_3$, and $R_4$ are hydrogen.

N-(Alk-2-ynyloxy)carbonylisoserine is then converted into corresponding ester in presence of an alcohol and an activating agent such as dicyclohexylcarbodiimide or carbonyldiimidazole. The most preferred alcohol is methanol and the most preferred activating agents is carbonyldiimidazole. The esterification can be carried out in various solvents such as dichloromethane, chloroform, ethyl acetate, tetrahydrofuran, acetonitrile or dimethyl-formamide. The most preferred solvent is acetonitrile. The esterification is carried out by first mixing acid with activating agent for 0.5–6 hr, most preferably for 1 hr, at 0–25° C., most preferably at 10° C. Then the alcohol is introduced in the mixture over a period of 10–60 min, most preferably over 30 min and the mixing is done for 1–6 hr, most preferably for 2 hr.

Methyl ester is alternatively prepared by condensing isoserine with diazomethane. The ethereal solution of diazomethane is prepared from following the standard procedure described in Vogel's Text book of Practical Organic Chemistry, 1989, page 432. The methylation is effected by mixing the solution of N-(alk-2-ynyloxy)carbonylisoserine in tetrahydrofuran with excess ethereal solution of diazomethane. The resultant mixture is stored for 1–6 hr, most preferably for 2 hr at 5–25° C., most preferably at 10° C., for complete reaction.

In the most preferred ester 14, $R_1$ is phenyl, $R_2$ $R_3$ and $R_4$ are hydrogen; and $R_5$ is methyl.

N-(alk-2-ynyloxy)carbonylisoserine ester 14 is converted into oxazolidine 15 in presence of chemical such as alkoxyalkene or gem-dialkoxyalkane or 1,1,1-trialkoxyalkane. These chemicals are basically reagents for protection of vicinal functional groups such as diols or amino/amidoalchohols in cyclic form. The appropriate chemical is chosen on the basis of type of protecting group required. The most preferred alkoxylalkene, 2-methoxypropene, is available commercially. The reactions are catalysed by p-arylsulfonic acid or their pyridinium salt. The most preferred catalyst is pyridinium p-toluenesulfonate. The protection with 2-methoxypropene results in formation of 3-(alk-2-ynyloxy)carbonyl-5-oxazolidine carboxylic ester 15. In the most preferred oxazolidine ester, $R_1$, $R_2$ and $R_3$ are hydrogen, $R_4$ is phenyl; $R_5$, $R_6$ and $R_7$ are methyl.

3-(Alk-2-ynyloxy)carbonyl-5-oxazolidine carboxylic ester is finally converted into corresponding acid, by hydrolysis with alkali hydroxide or carbonate and mineral acid used successively. The hydrolysis is effected by mixing of a solution of ester in alcohol with an Aq. alkali hydroxide. The most preferred alcohol is methanol and the most preferred alkali hydroxide is sodium hydroxide. The mixing is done for 1 to 6 hr, the most preferably for 3 hr. After the hydrolysis is over, the reaction mixture is acidified to pH 3–6, most preferably 4.5. The acid 16 is isolated by extraction with dichloromethane. In the most preferred acid, $R_1$, $R_2$, and $R_3$ are hydrogen, $R_4$ is phenyl; $R_5$ and $R_6$ are methyl.

There is also provided a process of preparation of taxol and synthetic taxol analogs from 3-(alk-2-ynyloxy) carbonyl-5-oxazolidine carboxylic acids and taxane alcohols, which can be derived from natural or unnatural sources having the following reaction as an example:

synthesized from baccatin and 10-deacetylbacctin respectively in presence of 2,2,2-trichloroethoxy chloroformate and organic base. The preferred bases are pyridine, 4-dimethylaminopyridine or imidazole or like. The most preferred base is pyridine.

The 3-(prop-2-ynyloxy)carbonyl-2, 2-dimethyl-4-phenyl-5 oxazolidine carboxylic acid 16 is converted into taxane ester 18 in presence of taxane alcohol such as 7-O-(2,2,2-trichloroethoxy)carbonylbaccatin 17 and con-

SCHEME-2

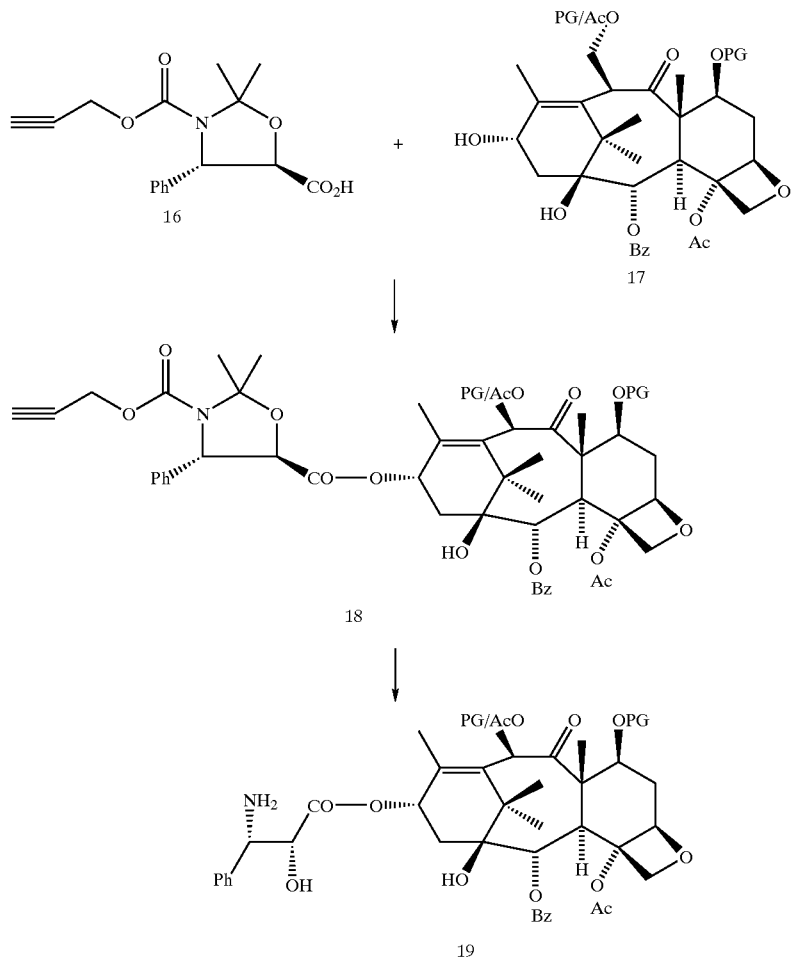

PG = Protecting groups

The most preferred 3-(alk-2-ynyloxy)carbonyl-5-oxazolidine carboxylic is 3-(prop-2-ynyloxy)carbonyl-2,2-dimethyl-4-phenyl-5-oxazolidine carboxylic acid. The preferred tetracyclic taxane alcohols are 7-O-triethylsilylbaccatin, 7-O-(2,2,2-trichloro-ethoxy) carbonylbaccatin, 7,10-di-O-(2,2,2-trichloroethoxy) carbonyl-10-deacetylbaccatin, 7, 10-di-O-benzyloxycarbonyl-10-deacetylbaccatin, 7-O-t-butyloxycarbonylbaccatin, 7,10-di-O-t-butyloxycarbonyl-10-deacetylbaccatin, 7-O-(prop-2-ynyloxy) carbonylbaccatin, and 7,10-di-O-(prop2-ynyloxy)carbonyl-10-deacetylbaccatin. The most preferred alcohols are 7-O-(2,2,2-trichloroethoxy)carbonylbaccatin, 7,10-di-O-( 2,2,2-trichloroethoxy)carbonyl-10-deacetylbaccatin.

7-O-(2,2,2-trichloroethoxy)carbonylbaccatin, 7,10-di-O-(2,2,2-trichloroethoxy)carbonyl-10-deacetylbaccatin are densing agent, preferably dicyclohexylcarbodiimde and organic base preferably 4-dimethylaminopyridine. This process can also be used to prepare various taxane esters 10 contemplated within the present invention from various 3-(alk-2-ynyloxy)carbonyl-5oxazolidine carboxylic acids and taxane alcohols.

The opening of the oxazolidine ring in ester 18 is effected by removal of prop-2-ynyloxy carbonyl with ammonium tetrathiomolybadate preferably benzyltriethyl ammonium tetrathiomolybadate which is prepared according to the known procedure described in Syn.Comm., 22(22), 3277–3284(1992). The removal of prop-2-ynyloxycarbonyl group is effected by exposing the mixture of ester and acetonitrile to ultrasound for 1–6 hr, most preferably for 3 hr. The reaction mixture is diluted with dichloromethane and then washed with water. Removal of the solvents gives the intermediate 19, free amine. The same procedure can be applied to prepare other free amino taxane intermediates 11 (where W is hydrogen) contemplated within the present invention.

The resultant free amine can then be converted into taxol 1 or non-natural taxols such as 2 and 11 contemplated within the present invention following the known methods as illustrated in scheme-3

SCHEME-3

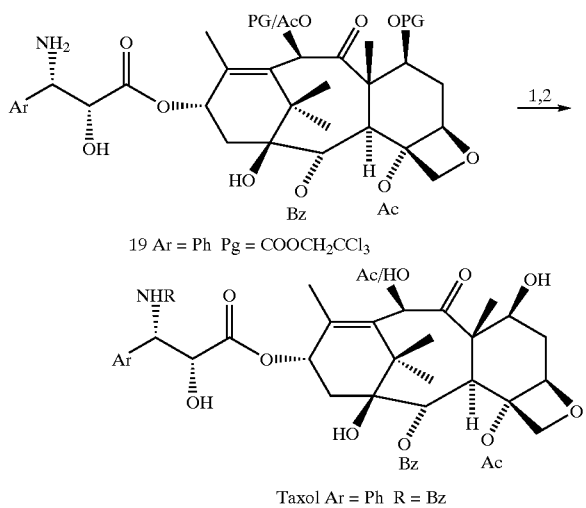

19 Ar = Ph Pg = COOCH$_2$CCl$_3$

Taxol Ar = Ph  R = Bz
1. Acylation of Amine
2. Deprotection of Protecting groups The invention will now be explained in greater details with the help of the accompanying examples:

EXAMPLE 1

(2R, 3S) phenylisoserine (25 gm, 0.138 mole) was dissolved in sodium bicarbonate and potassium bicarbonate (2.5 L) and then 0–5° C. Prop-2-ynyl chloroformate (25 gm, 0.21 mmol) was added drop wise into the solution in a period of 10 to 15 mins. After complete addition the reaction mixture was stirred for 6 Hrs at 05° C. pH of the solution was brought down to 4 by drop wise addition of 10% hydrochloric acid, at temperature 5–6° C. The acidified aqueous layer was extracted with a mixture of tetrahydrofuran and dichloromethane (4:1, 3×1L). The combined organic layer was washed with water until the neutral pH.

The organic layer was dried over sodium sulphate and filtered evaporated in under vacuum below 40° C. The residue was dried in vacuum until constant weight to yield 20 g of compound 13.

EXAMPLE 2

To a ice cooled solution of Comp-13 (20 g, 76 mmol) in tetrahydrofuran (500 ml) was added drop wise a saturated ethereal solution of diazomethane. The addition was continued until the colour of diazomethane persists. Stirring was continued for further 2 Hrs. The excess diazomethane was removed by drop wise addition of acetic acid. The react-ion mixture was then washed with 7 solution of sodium bicarbonate. The organic layer was washed with brine and dried over sodium sulfate. The organic layer was filtered and evaporated. The crude product was purified over silica gel (230–400) (eluent; hexane-ethyl acetate, 7:3 to 1:1) yield comp-14 (18 gm).

EXAMPLE 3

To a stirred solution of Comp 13 (5.0 g, 19 mmol) in tetrahydrofuran (50 ml) was added 1,1 carbonyl diimidazole (6.2 gm, 38 mmol) at 0–10° C. The stirring was continued for further 1 Hr. Methanol (3.2 ml) was then added drop wise into the solution in a period of 30 min. After complete addition, the reaction mixture was stirred for 2 Hr, when T.L.C. indicated completion of the reaction. The reaction mixture was concentrated and the residue dissolved in ethyl acetate (2×100 ml), washed with 5% hydrochloric acid, water and brine. The organic layer was dried and evaporated. The crude product was chromatograph over silica gel (eluent hexane: ethyl acetate 7:3 to 1:1) yield to comp 14 (4.5 gm).

EXAMPLE 4

To a stirred solution of Comp-14 (5 g 18 mmol) in toluene (180 ml) was added 2-methoxypropene (35 ml, 0.36 mole), and pyridinium p-toluenesulfonate (425 mg). The mixture was stirred at 25° C. for 10–15 min and then heated 80° C. for 6 Hr. Progress of the reaction was checked by T.L.C. After completion, the reaction, mixture was cooled and diluted with ethyl acetate (300 ml). The organic layer was washed with 5% sodium bicarbonate (2×125 ml) then with brine (150 ml). The organic layer was dried over sodium sulfate. After filtration, the organic layer was evaporated in rotavapour under vacuum below 40° C. The crude product was purified by column chromatography over silica gel, 240–400 mesh (eluent lower 85:15 hexane and ethyl acetate to yield comp-15, (3 g) as a colourless oil.

EXAMPLE 5

To a stirred solution of comp-15 (3.5 g, 11 mmol) in methanol (35 ml) was added a solution of lithium hydroxide (1.8 g) in water (15 ml). After stirring at 20–25° C. for 3 Hr (absence of starting material, was checked by T.L.C.). The reaction mixture was concentrated to reduce the volume to 15 ml and diluted with dichloromethane (200 ml). The mixture was then washed with water (250 ml). The aqueous layer was separated and cooled to 5–15° C. and solution pH was brought to 4 by adding 10% hydrochloric acid. The aqueous layer as extracted with or dichloromethane (3×300 ml). The combined organic layer was washed with brine and dried over, preferably sodium sulfate and magnesium sulfate. After filtration the organic layer was evaporated under vaccum and residue was dried up to constant weight to yield compound-16 (2.2 gm) .

EXAMPLE 6

To a stirred solution of comp-16 (2.0 g, 6.6 mmol) in toluene or (20 ml) was added dicyclohexylcarbodiimide (3 g) followed by addition of 7-O-trichloroethoxycarbonylbaccatin 17, (2 g, 2.62 mmol) and DMAP (101 mg). The stirring was continued for 1 Hr. The reaction mixture was diluted with ethyl acetate (100 ml) and filtered. The filtrate was washed successively with aqueous saturated sodium bicarbonate and brine. The organic layer was dried and evaporated under vaccum. The crude product was purified over silica gel (eluent 4:1 hexane and ethyl acetate) to yield comp-18 (1.9 g).

EXAMPLE 7

A mixture of comp-18 (2 g, 1.91 mmol) and benzyl triethyl-ammonium tetrathiomolybedate (1.16 g) in acetonitrile (5 ml) was kept in ultrasound bath for 4 hr and then diluted with dichloromethane (30 ml). The mixture was washed with water (2×10 ml). The organic layer was evaporated to give comp-19 (1.75 g) as solid.

EXAMPLE 8

A mixture of comp-19 (1 g, 1.08 mmol) in ethyl acetate (5 mL) and saturated Aq. sodium bicarbonate (3 mL) was added benzoyl chloride (0.17 mL) in ethyl acetate (2 mL) drop wise at 0° C. After, the complete addition, the temperature was raised to 25° C. and the stirring was continued for further 2 hr. The Aq. layer was separated and the organic layer was washed with water until neutral. The organic layer was dried over sodium sulfate and then evaporated to give a solid. A mixture of this solid, acetic acid (10 mL), methanol (5 mL) and zinc powder (1 g) was heated to 60° C. with stirring. After 1 hr, the reaction mixture was cooled and then filtered. The filtrate was evaporated. The residue was dissolved in ethyl acetate and then washed with Aq. sodium bicarbonate, water and brine. The organic layer was dried over sodium sulfate, then filtered and evaporated. The solid residue was crystallised with acetone-hexane then with methanol-water to afford Taxol (0.74 g, yield 80% from comp-18 99% HPLC w/w assay, 99% HPLC chromatographic purity).

We claim:

1. A 3-(alk-2-ynyloxy)carbonyl-5-oxazolidine carboxylic acid and its analogs having a structural formula:

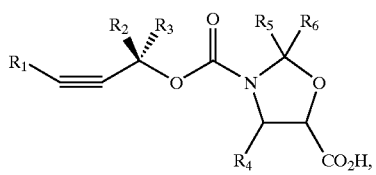

wherein $R_1$ is selected from the group consisting of hydrogen, aryl, heteroaryl, alkyl, alkenyl, and alkynyl, wherein $R_2$ and $R_3$ are independently selected from the group consisting of hydrogen, alkyl, alkenyl, alkynyl, aryl, and heteroaryl, wherein $R_4$ is selected from the group consisting of hydrogen, alkyl, alkenyl, alkynyl, aryl substituted aryl, and heteroaryl, and wherein $R_5$ and $R_6$ are independently selected from the group consisting of hydrogen, alkyl, alkenyl, alkynyl, aryl, heteroaryl, alkoxy, alkyloxy, alkynyloxy, aryloxy, and heteroaryloxy.

2. The 3-(alk-2-ynyloxy)carbonyl-5-oxazolidine carboxylic acid and its analogs as claimed in claim 1 having a structural formula:

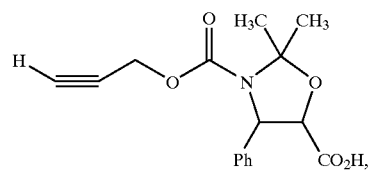

wherein $R_1$ is hydrogen, wherein $R_2$ and $R_3$ are hydrogen, wherein $R_4$ is phenyl, and wherein $R_5$ and $R_6$ are methyl.

3. A taxol intermediate, a natural taxol, and a non-naturally-occurring taxol having a structural formula:

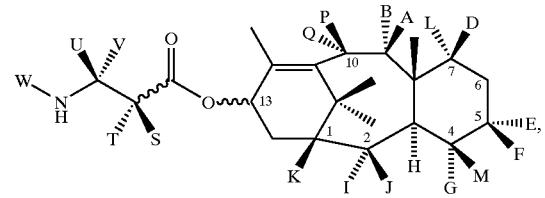

wherein A and B are one of (a) independently selected from the group consisting of hydrogen, lower alkanoyloxy, alkenoyloxy, alkynoyloxy, and aryloyloxy or (b) A and B together form an oxo group;

wherein L and D are independently selected from the group consisting of hydrogen, hydroxy, lower alkanoyloxy, alkenoyloxy, alkynoyloxy, aryloyloxy, alkoxycarbonyloxy, arloxycarbonyloxy, and alkylsilyloxy;

wherein E and F are one of (a) independently selected from the group consisting of hydrogen, lower alkanoyloxy, alkenoyloxy, alkynoyloxy, and aryloyloxy or (b) E and F together form an oxo group;

wherein G is one of (a) selected from ther group consisting of hydrogen, hydroxy, lower alkanoyloxy, alkenoyloxy, alkynoyloxy, and aryloyloxy or (b) G and M together form a ring selected from the group consisting of an oxo ring, a methylene ring, and an oxirane ring or wherein M and F together form an oxetane ring;

wherein J is selected from the group consisting of hydrogen, hydroxy, lower alkanoyloxy, alkenoyloxy, alkynoyloxy, and aryloyloxy; or I is one of (a) selected from the group consisting of hydrogen, hydroxy, lower alkanoyloxy, alkenoyloxy, alkynoyloxy, and aryloyloxy or (b) I and J together form an oxo group;

wherein K is selected from the group consisting of hydrogen, hydroxy, lower alkoxy, alkanoyloxy, alkenoyloxy, alkynoyloxy, and aryloyloxy;

wherein P and Q are one of (a) independently selected from the group consisting of hydrogen, hydroxy, lower alkanoyloxy, alkenoyloxy, alkynoyloxy, aryloyloxy, alkoxycarbonyloxy, aryloxycarbonyloxy, and alkylsilyloxy or (b) P and Q together form an oxo group;

wherein S and T are independently selected from the group consisting of hydroxy, alkoxy, aryloxy, lower alkanoyloxy, alkenoyloxy, alkynoyloxy, and aryloyloxy;

wherein U and V are independently selected from the group consisting of hydrogen, lower alkyl, alkenyl, alkynyl, aryl, substituted aryl, and heteroaryl; and wherein W is selected from the group consisting of hydrogen, alkanoyl, alkenoyl, alkynoyl, aryloyl, heteroaryloyl, alkoxycarbonyl, aryloxycarbonyl, and heteroaryloxycarbonyl.

4. A taxol intermediate having a structural formula:

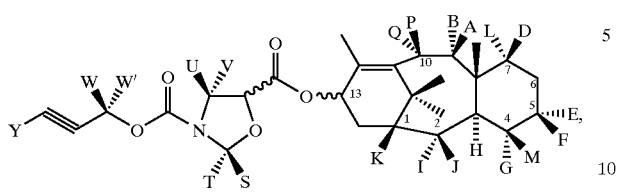

wherein A and B are one of (a) independently selected from the group consisting of hydrogen, lower alkanoyloxy, alkenoyloxy, alkynoyloxy, and aryloyloxy or (b) A and B together form an oxo group;

wherein L and D are independently selected from the group consisting of hydrogen, hydroxy, lower alkanoyloxy, alkenoyloxy, alkynoyloxy, aryloyloxy, alkoxycarbonyloxy, aryloxycarbonyloxy, and alkylsilyloxy;

wherein E and F are one of (a) independently selected from the group consisting of hydrogen, lower alkanolyloxy, alkenoyloxy, alkynoyloxy, and aryloyloxy or (b) E and F together form an oxo group;

wherein G is one of (a) selected from the group consisting of hydrogen, hydroxy, lower alkanoyloxy, alkenoyloxy, alkynoyloxy, aryloyloxy, and aryloyloxy or (b) G and M together form a ring which is one of an oxo ring, a methylene ring, or an oxirane ring; or wherein M and F together form an oxetane ring;

wherein J is selected from the group consisting of hydrogen, hydroxy, lower alkanoyloxy, alkenoyloxy, alkynoyloxy, and aryloyloxy; or wherein I is one of (a) selected from the group consisting of hydrogen, hydroxy, lower alkanoyloxy, alkenoyloxy, alkynoyloxy, and aryloyloxy or (b) I and J together form an oxo group; and wherein K is selected from the group consisting of hydrogen, hydroxy, lower alkoxy, alkanoyloxy, alkenoyloxy, alkynoyloxy, and aryloyloxy;

wherein P and Q are one of (a) independently selected from the group consisting of hydrogen, hydroxy, lower alkanoyloxy, alkenoyloxy, alkynoyloxy, aryloyloxy, alkoxycarbonyloxy, aryloxycarbonyloxy, and alkylsilyloxy or (b) P and Q together form an oxo;

wherein S and T are independently selected from ther group consisting of hydrogen, lower alkyl, alkoxy, alkenyl, alkynyl, aryl, aryloxy, substituted aryl, and substituted aryloxy;

wherein U and V are independently selected from the group consisting of hydrogen, lower alkyl, alkenyl, alkynyl, aryl, and substituted aryl;

wherein W and $W^1$ are independently selected from the group consisting of hydrogen, lower alkyl, aryl, and substituted aryl; and wherein Y is selected from the group consisting of hydrogen, lower alkyl, aryl, and substituted aryl.

5. The taxol intermediate as claimed in claim 4, wherein the taxol alkyl groups either alone or with variable substituents defined in claim 4 are one of (a) lower alkyl groups containing from one to six carbon atoms in a principal chain or (b) alkyl groups containing up to 10 carbon atoms, and comprise chain structures which are one of straight or branched.

6. The taxol intermediate as claimed in claim 4, wherein the taxol alkenyl groups either alone or with various substituents defined in claim 4 are one of (a) lower alkenyl groups containing from two to six carbon atoms in a principal chain or (b) alkenyl groups containing up to 10 carbon atoms, and comprise a straight chain.

7. The taxol intermediate as claimed in claim 4, wherein the taxol alkynyl groups, either along or with various substituents defined in claim 4 one of (a) lower alkynyl groups containing from two to six carbon atoms in a principal chain or (b) alkynyl groups containing up to 10 carbon atoms, and comprise a straight chain.

8. The taxol intermediate as claimed in claim 4, wherein the taxol aryl moieties, either alone or with various substituents defined in claim 4 contain from 6 to 10 carbon atoms, wherein the taxol aryl moieties include at least one group selected from the group consisting of phenyl and naphthyl, and wherein the taxol aryl moieties include at least one substituent selected from the group consisting of alkanoxy, hydroxy, halogen, alkyl, aryl, alkenyl, acyl, acyloxy, nitro, amino, and amido.

9. A process for preparing a 3-(alk-2-ynyloxy)carbonyl-5-oxazolidine carboxylic acid a defined in claim 1 having a reaction sequence as follows:

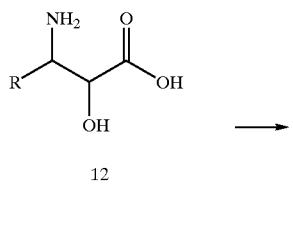

12

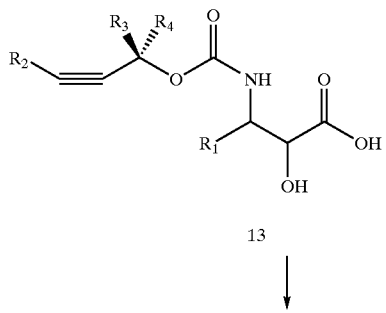

13

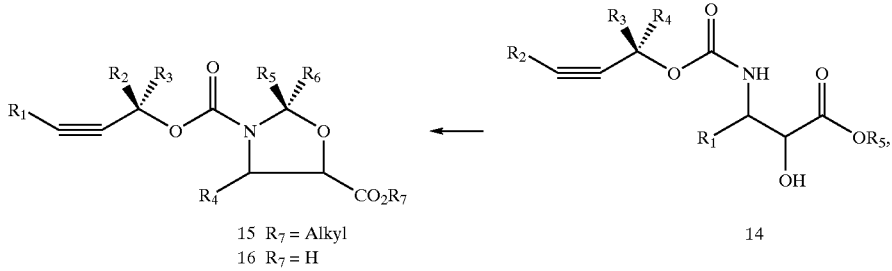

15  R₇ = Alkyl
16  R₇ = H the process comprising the steps of:
condensing isoserine of formula 12 with alk-2-ynyl haloformate in the presence of a base to produce N-(alk-2-ynyloxy)carbonylisoserine of formula 13;
esterifying the N-(alk-2-ynyloxy)carbonlyisoserine into a corresponding ester of formula 14 in the presence of alcohol;
converting the corresponding ester into oxazolidine ester of formula 15; and
converting the oxazolidine ester by ester hydrolysis to produce the corresponding acid of formula 16.

10. The process as claimed in claim 9, wherein R in formula 12 is aryl, wherein the arylisoserine has two asymmetric carbons, and wherein the arylisoserine has an optically active form.

11. The process as claimed in claim 10, wherein R in formula 12 is phenyl, and wherein the pheneylisoserine has an optically active form which is 2R, 3S.

12. The process as claimed in claim 9, wherein condensing is carried out by addition of chloroformate into a solution of isoserine in aqueous bicarbonate over a period of 5–30 min.

13. The process as claimed in claim 12, wherein condensing is carried out over a period of 10–15 min.

14. The process as claimed in claim 9, wherein esterifying the compound of formula 13 into a corresponding ester is conducted in the presence of an alcohol and an activating agent.

15. The process as claimed in claim 14, wherein the activating agent is selected from the group consisting of dicyclohexylcarbodiimide and carbonyldiimidazole.

16. The process as claimed in claim 14, wherein esterifying is carried out by first mixing an acid with the activating agent for a time period ranging from 0.5–6 hr and at a temperature ranging from 0–25° C. to obtain a mixture, wherein alcohol is introduced into the mixture over a time period ranging from 10–60 min, and wherein mixing is performed for a time period of 16 hr.

17. The process as claimed in claim 16, wherein esterifying is carried out by first mixing an acid with the activating agent for a time period of 1 hr and at a temperature of 10° C. to obtain a mixture, wherein alcohol is introduced into the mixture over a period of 30 min., and wherein mixing is performed for 2 hr.

18. The process as claimed in claim 9, wherein converting the oxazolidine ester into a corresponding acid by ester hydrolysis is performed by successively hydrolyzing with one of alkali hydroxide or carbonate and acidifying with a mineral acid.

19. The process as claimed in claim 18, wherein hydrolyzing is effected by mixing a solution of the oxazolidine ester in alcohol with an aqueous alkali hydroxide.

20. A process for preparation of one of a taxol or a synthetic taxol analog having a reaction sequence as follows:

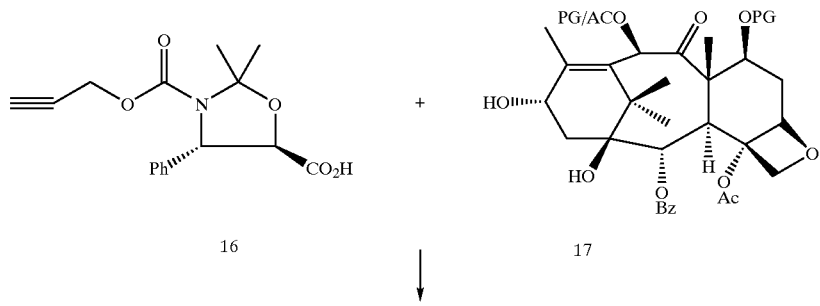

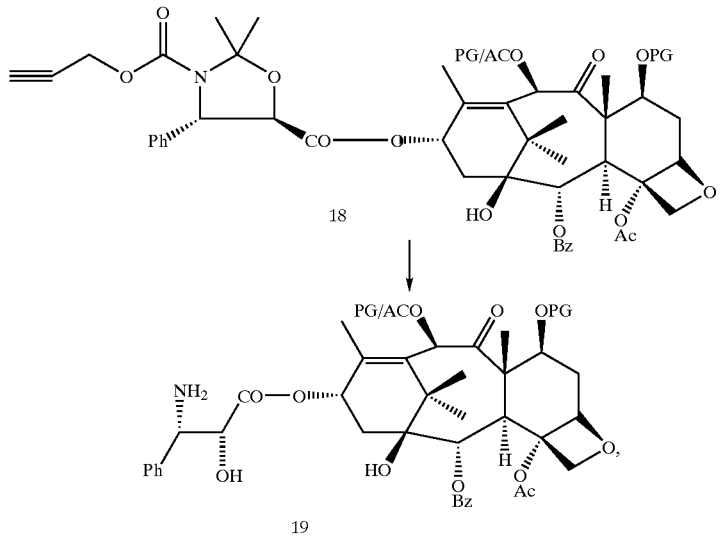

the process comprising the steps of:
  condensing an oxazolidine carboxylic acid of formula 16 with taxane alcohol of formula 17 using a condensing agent and an organic base to produce an ester of formula 18;
  treating the ester of formula 18 with tetrathiomolybadate to produce an amine of formula 19; and
  converting the amine of formula 19 into one of the taxol or the synthetic taxol analog.

21. The process as claimed in claim 20, wherein the condensing agent is dicycohexylcarbodiimde.

22. The process as claimed in claim 20, wherein the organic base is 4-dimethylaminopyridine.

23. The process as claimed in claim 20, wherein the taxane alcohol is 7-O-(2,2,2-trichloroethoxy)carbonylbaccatin.

24. The process as claimed in claim 20, wherein the oxazolidine carboxylic acid is 3-(prop-2-ynyloxy)carbonyl-2,2-dimethyl-5-oxazolidine carboxylic acid.

25. The process as claimed in claim 20, wherein the tetrathiomolybadate is a prop-2-ynyloxy carbonyl group cleaving reagent and is benzyltriethyl-ammonium tetrathiomolybadate.

* * * * *